(12) United States Patent
Woehr et al.

(10) Patent No.: US 7,608,057 B2
(45) Date of Patent: *Oct. 27, 2009

(54) PROTECTIVE DEVICE FOR AN INJECTION NEEDLE

(75) Inventors: Kevin Woehr, Felsberg (DE); Juergen Fuchs, Bad Emstal (DE); Kenneth C. Raines, Bethlehem, PA (US); Joel M. Bartholomew, Danielsvile, PA (US)

(73) Assignee: B. Braun Meisungen AG, Meisungen (DE)

( * ) Notice: Subject to any disclaimer, the term of this patent is extended or adjusted under 35 U.S.C. 154(b) by 230 days.

This patent is subject to a terminal disclaimer.

(21) Appl. No.: 11/609,772

(22) Filed: Dec. 12, 2006

(65) Prior Publication Data

US 2007/0083159 A1   Apr. 12, 2007

Related U.S. Application Data

(60) Division of application No. 11/537,368, filed on Sep. 29, 2006, which is a division of application No. 10/856,315, filed on May 27, 2004, now Pat. No. 7,125,397, which is a continuation-in-part of application No. 10/468,923, filed on Feb. 2, 2004, now Pat. No. 7,214,211, which is a continuation-in-part of application No. 10/445,166, filed on May 23, 2003, now Pat. No. 7,264,613, which is a continuation of application No. 09/638,641, filed on Aug. 14, 2000, now Pat. No. 6,616,630, which is a continuation-in-part of application No. 09/183,697, filed on Oct. 30, 1998, now Pat. No. 6,287,278, which is a continuation-in-part of application No. 09/097,170, filed on Jun. 12, 1998, now Pat. No. 6,117,108, which is a continuation-in-part of application No. 08/915,148, filed on Aug. 20, 1997, now abandoned.

(30) Foreign Application Priority Data

Feb. 26, 2001  (DE) ............................... 201 03 363
Feb. 26, 2002  (WO) ....................... PCT/EP02/02042

(51) Int. Cl.
  *A61M 5/00* (2006.01)
  *A61M 5/32* (2006.01)
(52) U.S. Cl. .................. 604/110; 604/192; 604/198
(58) Field of Classification Search ................ 604/110, 604/192–198, 263, 164.08, 162, 164.01, 604/164.107
See application file for complete search history.

(56) References Cited

U.S. PATENT DOCUMENTS 5,344,408 A * 9/1994 Partika ..................... 604/192

(Continued)

*Primary Examiner*—Matthew F Desanto
(74) *Attorney, Agent, or Firm*—Klein, O'Neill & Singh, LLP

(57) ABSTRACT

Protective devices for injection needles or infusion needles that include a needle holder at a proximal end of the needle, on whose shaft a protective element for the needle tip can be positioned and moved, are herein disclosed. The protective element is configured to block the needle tip following an injection to prevent accidental contact therewith. The protective element may be positioned on the shaft in a ready to use position inside a grip part or middle retaining portion, which is also used to activate the protective element over the needle following the injection.

17 Claims, 10 Drawing Sheets

U.S. PATENT DOCUMENTS

| | | | |
|---|---|---|---|
| 5,348,544 A * | 9/1994 | Sweeney et al. | 604/192 |
| 6,425,884 B1 * | 7/2002 | Wemmert et al. | 604/162 |
| 6,749,588 B1 * | 6/2004 | Howell et al. | 604/164.08 |
| 7,125,397 B2 * | 10/2006 | Woehr et al. | 604/198 |
| 7,214,211 B2 * | 5/2007 | Woehr et al. | 604/164.08 |

* cited by examiner

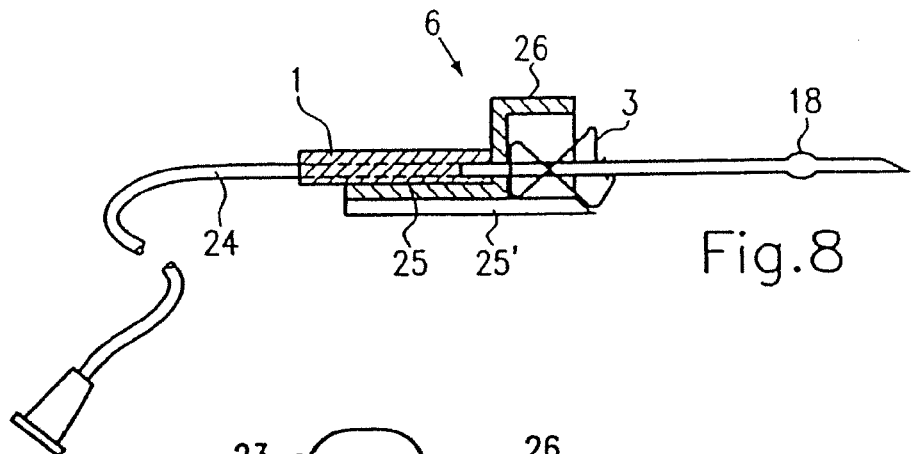
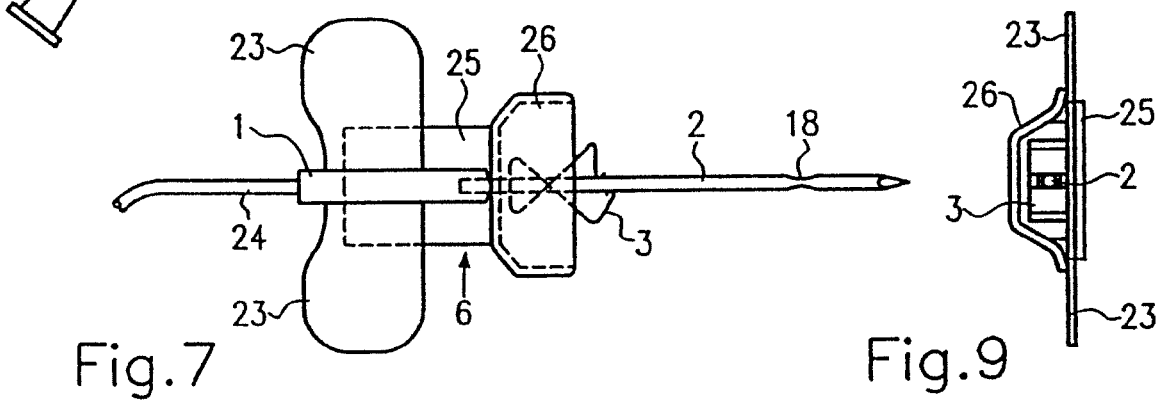
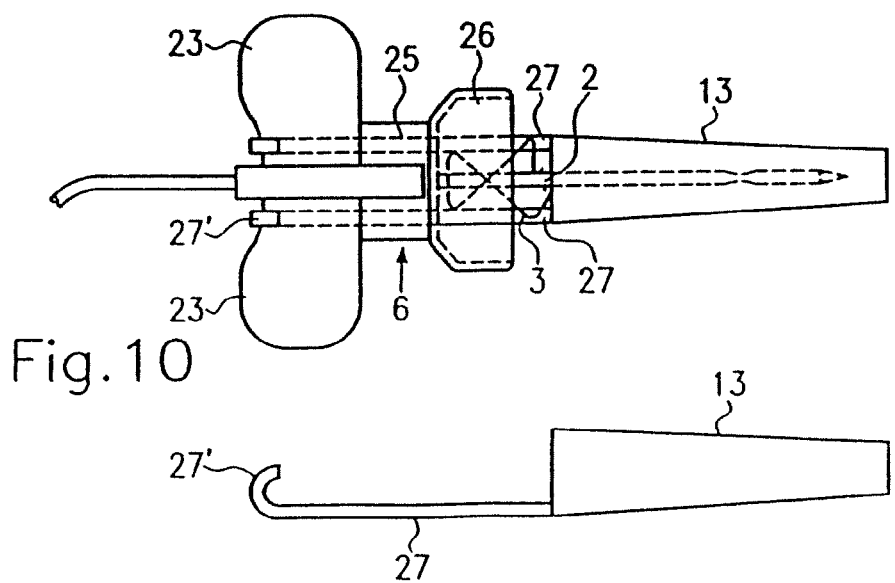

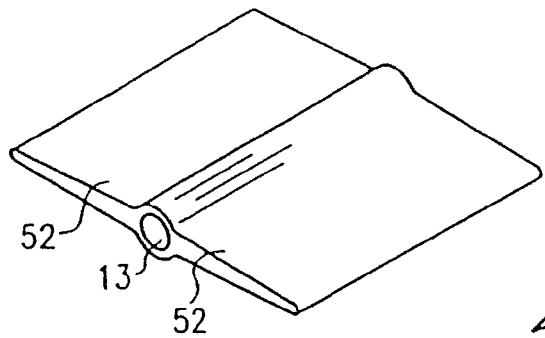
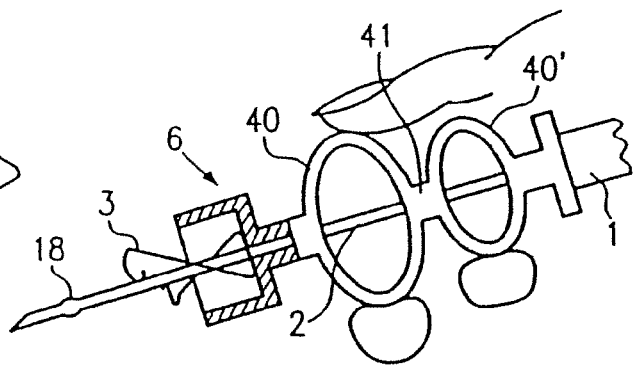
Fig.16a  Fig.17
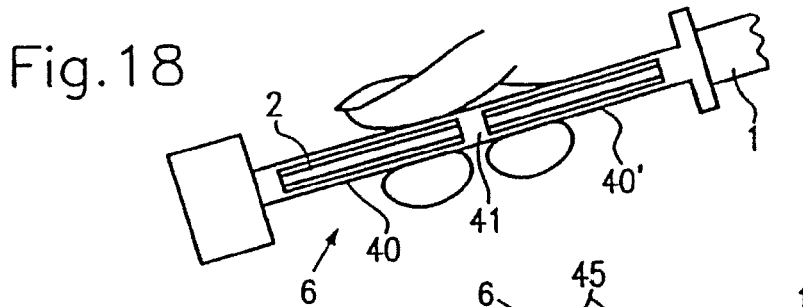
Fig.18
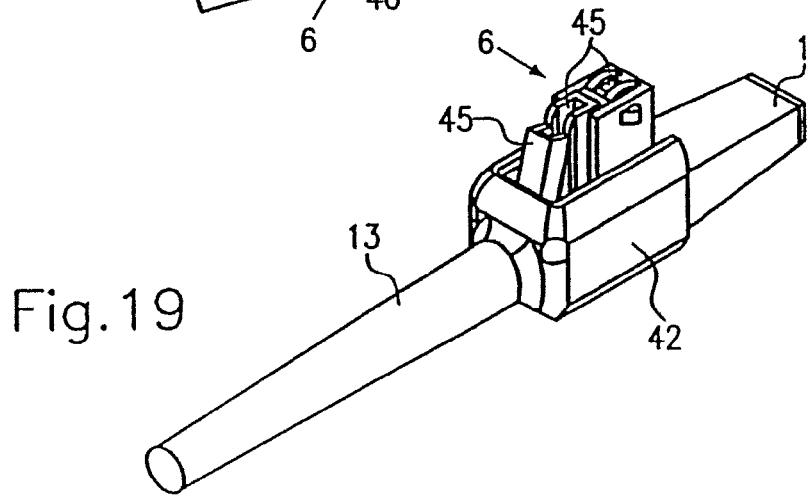
Fig.19
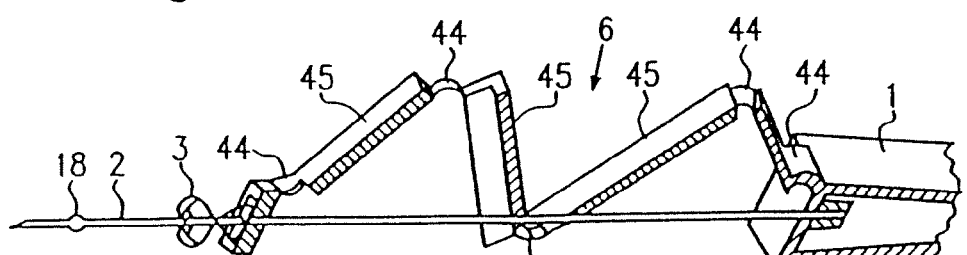
Fig.20

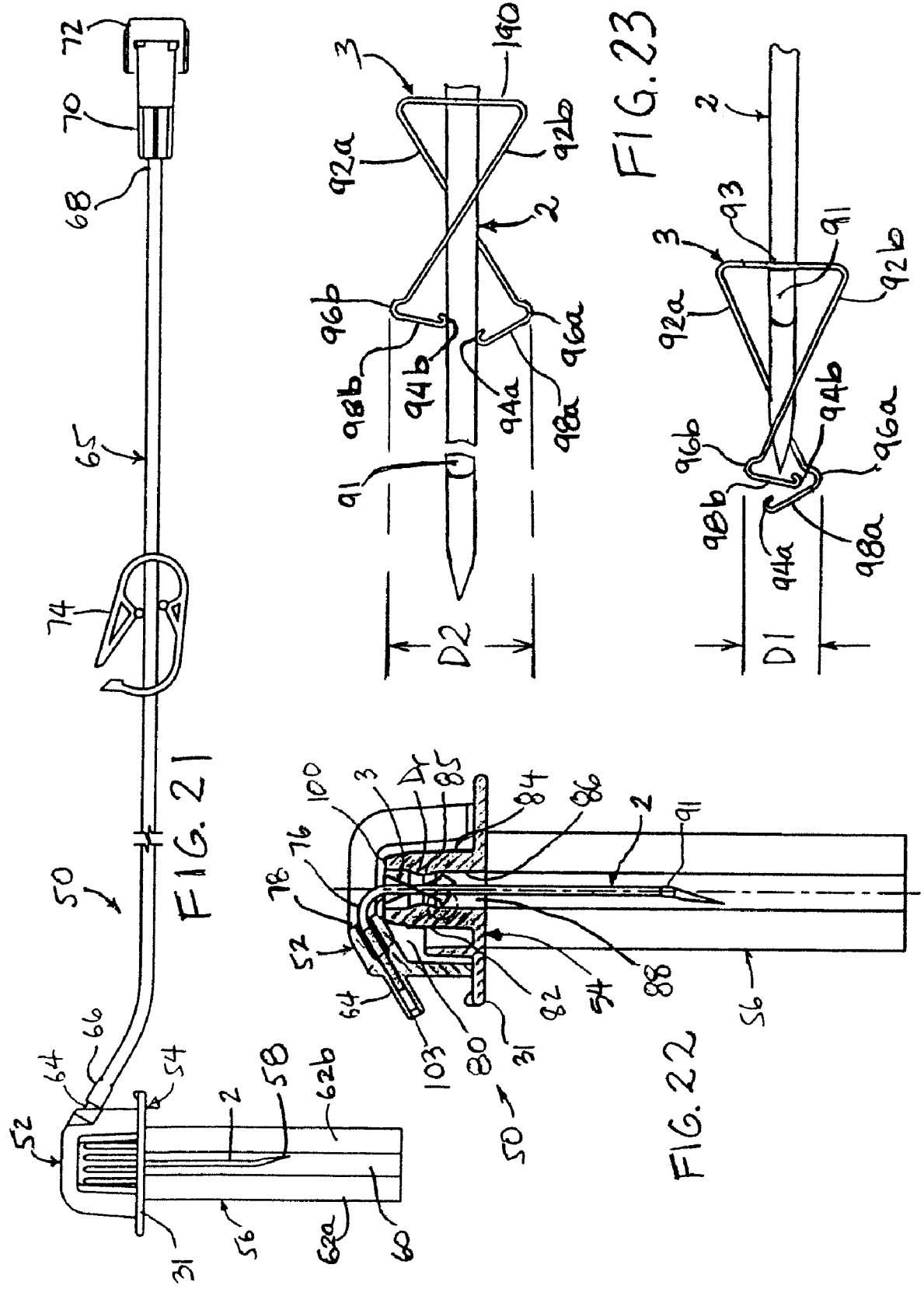

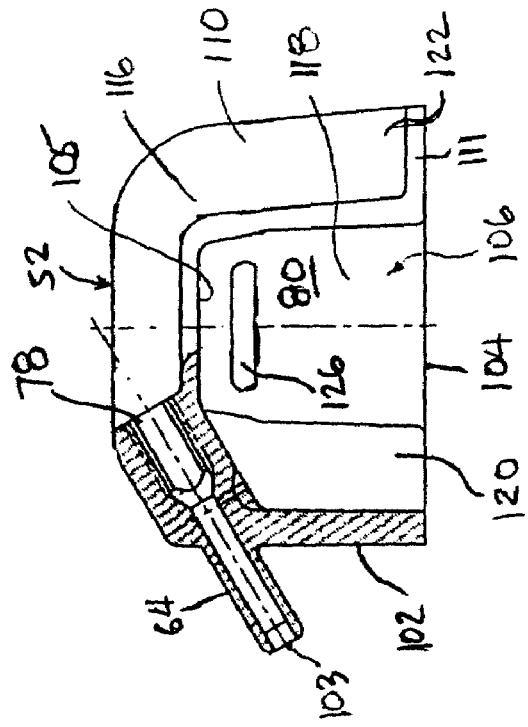
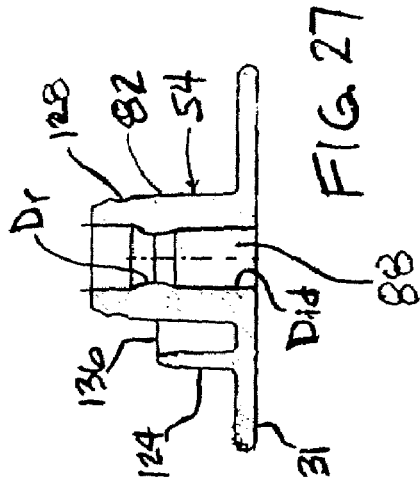
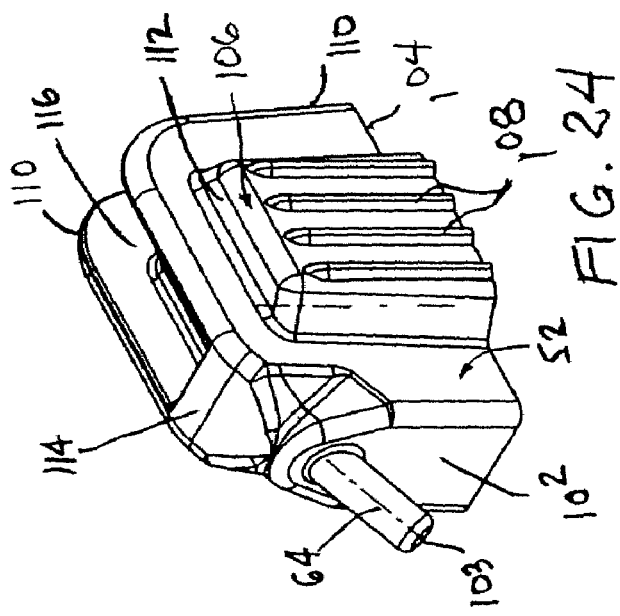
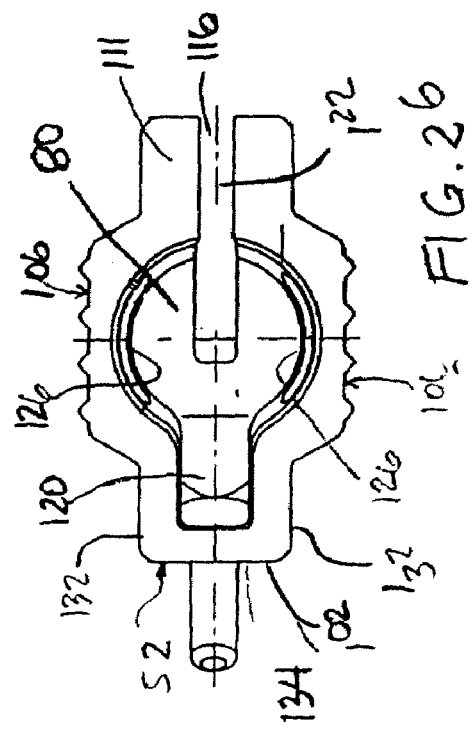

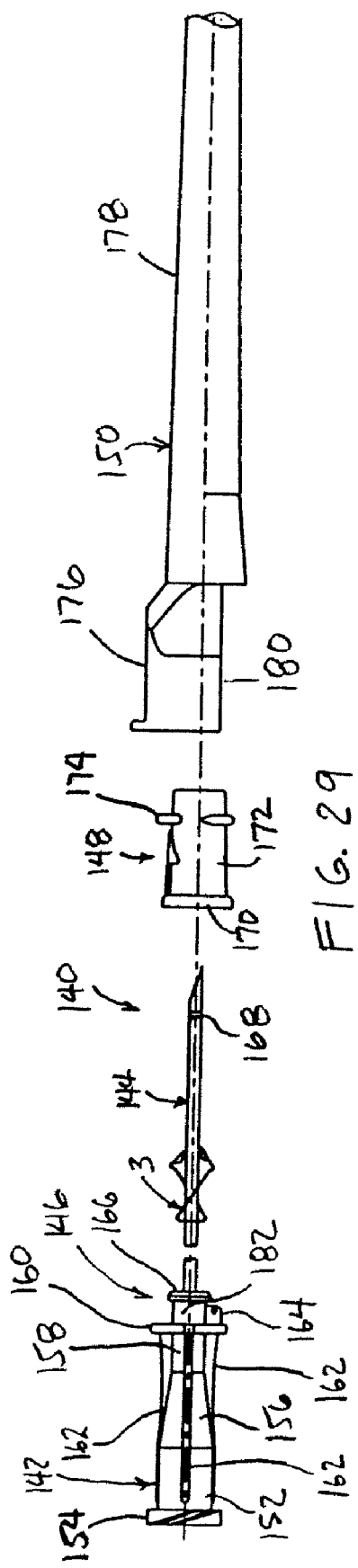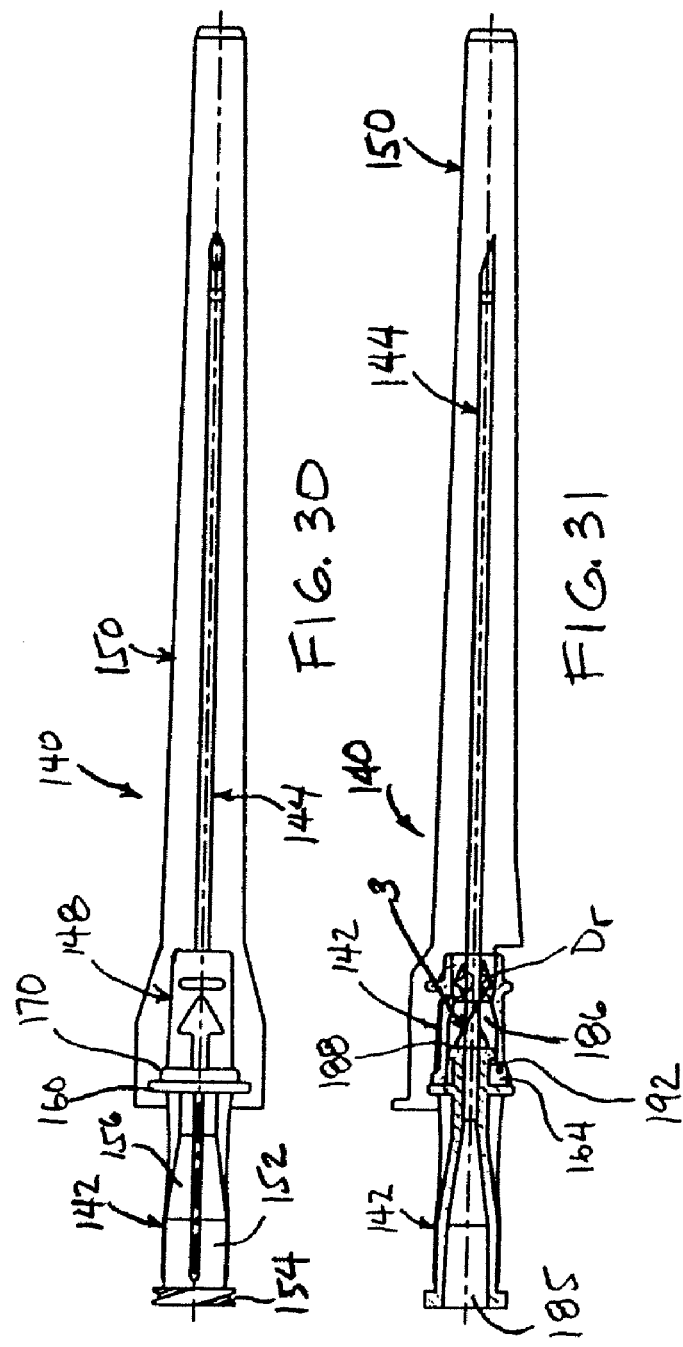

PROTECTIVE DEVICE FOR AN INJECTION NEEDLE

CROSS-REFERENCE TO RELATED APPLICATIONS

This application is a divisional application of Ser. No. 11/537,368; filed Sep. 29, 2006, which is a divisional application of Ser. No. 10/856,315, filed May 27, 2004, now U.S. Pat. No. 7,125,397 which is a continuation-in-part of an application entitled PROTECTIVE DEVICE FOR AN INJECTION NEEDLE, application Ser. No. 10/468,923, filed Feb. 2, 2004, now U.S. Pat. No. 7,214,211 which claims priority to international application No. PCT/EP02/02042, entitled PROTECTIVE DEVICE FOR AN INJECTION NEEDLE, filed Feb. 26, 2002, which claims the benefit of German application No. 201 03 363, filed Feb. 26, 2001, and also a continuation-in-part of an application entitled SPRING CLIP SAFETY IV CATHETER, application. Ser. No. 10/445,166, filed May 23, 2003, now U.S. Pat. No. 7,264,613 which is a continuation of application Ser. No. 09/638,641, filed Aug. 14, 2000, now U.S. Pat. No. 6,616,630, which is a continuation-in-part of application Ser. No. 09/183,697, filed Oct. 30, 1998, now U.S. Pat. No. 6,287,278, which is a continuation-in-part of application Ser. No. 09/097,170, filed Jun. 12, 1998, now U.S. Pat. No. 6,117,108, which is a continuation-in-part of application Ser. No. 08/915,148, filed Aug. 20, 1997, now abandoned, the contents of which are expressly incorporated herein by reference.

BACKGROUND

Protective devices for covering needle tips are well known, for example from U.S. Pat. No. 4,929,241, wherein a relatively small protective element is arranged on a needle and can be moved by a spring from a retracted or ready position to a protected position on the needle tip. The elastic arms of the protective element engage over the needle tip while an engagement device on the protective element holds the latter on the needle shaft. Because of the relatively small size of the protective element, it is difficult to move it by hand on the needle. In addition, the securing spring can only be released when the needle tip lies free so that a risk of injury cannot be ruled out.

Accordingly, there is a need for a needle assembly that has an easy to use grip part for moving the protective element, which is positioned between the protective element and the needle holder or hub.

SUMMARY

The present invention may be implemented by providing a needle assembly comprising a needle holder comprising a body comprising a channel extending at least a portion of the body, an interior cavity in communication with the channel; a needle holding sleeve, and a Huber needle comprising a needle shaft attached to the needle holding sleeve; said Huber needle comprising a bent section along a portion of the needle shaft; a middle retaining portion removably received in the interior cavity of the needle holder, the middle retaining portion comprising a flange, a tubular projection, and a bore extending through the tubular projection and the flange having the Huber needle extending through the bore; said bore comprising a first section comprising a first dimension and a second section comprising a second dimension; and a protective element coaxially disposed with the needle shaft and positioned inside the bore; said protective element comprising a distal portion comprising a third dimension when positioned inside the bore and a fourth dimension when separated from the bore. In one exemplary embodiment, the first dimension is larger than the third dimension, which is larger than the second dimension, which is larger than the fourth dimension.

In another aspect of the present invention, there is provided a needle assembly comprising a needle holder comprising a body comprising a channel extending at least a portion of the body, an interior cavity in communication with the channel, a needle holding sleeve, and a Huber needle comprising a needle shaft attached to the needle holding sleeve; said Huber needle comprising a bent section along a portion of the needle shaft and a needle tip; a middle retaining portion removably received in the interior cavity of the needle holder comprising a flange, a tubular projection, a bore extending through the tubular projection and the flange, and the Huber needle extending through the bore; said bore comprising a wall surface comprising a wall engagement structure; and a protective element coaxially disposed with the needle shaft and positioned inside the bore; said protective element engaging the wall engagement structure of the bore when the Huber needle is moved relative to the middle retaining portion. In one exemplary embodiment, the protective element is disengaged from the wall engagement structure of the bore when the needle tip moves from a position distal of a finger portion of the protective element to a position proximal of the finger portion of the protective element.

In yet another aspect of the present invention, there is provided a needle assembly comprising a needle hub comprising a base section, a nose section, an exterior surface, and a interior surface defining an interior cavity; a needle comprising a needle shaft, a distal end comprising a needle tip, and a proximal end attached to the nose section of the needle hub; a middle retaining portion telescopically disposed over at least a portion of the nose section of the needle hub comprising a body structure comprising an exterior surface and an interior surface defining a bore; said bore comprising a wall surface comprising a wall engagement structure; and a protective element coaxially disposed with the needle shaft and positioned at least partially inside the bore of the middle retaining portion; said protective element engaging the wall engagement structure of the bore when the needle is moved relative to the middle retaining portion. In one exemplary embodiment, the protective element is disengaged from the wall engagement structure of the bore when the needle tip moves from a position distal of a finger portion of the protective element to a position proximal of the finger portion of the protective element.

In still yet another aspect of the present invention, there is provided a needle assembly comprising a needle hub comprising a base section, a nose section, an exterior surface, and a interior surface defining an interior cavity; a needle comprising a needle shaft, a distal end comprising a needle tip, and a proximal end attached to the nose section of the needle hub; a middle retaining portion telescopically disposed over at least a portion of the nose section of the needle hub comprising a body structure comprising an exterior surface and an interior surface defining a bore; said bore comprising a first section comprising a first dimension and a second section comprising a second dimension; and a protective element coaxially disposed with the needle shaft and positioned at least partially inside the bore of the middle retaining portion; said protective element comprising a distal portion comprising a third dimension when positioned inside the bore and a fourth dimension when separated from the bore. In one exemplary embodiment, the first dimension is larger than the third dimension, which is larger than the second dimension, which is larger than the fourth dimension.

BRIEF DESCRIPTION OF THE DRAWINGS

These and other features and advantages of the present invention will become appreciated as the same become better understood with reference to the specification, claims and appended drawings wherein:

FIG. 7 shows an embodiment in conjunction with a needle holder provided with wings;

FIG. 8 shows a cross section through the embodiment according to FIG. 7;

FIG. 9 shows an end view of FIG. 7;

FIG. 10 shows a plan view of an embodiment according to FIG. 7 with needle cap;

FIG. 11 shows a view of the needle cap according to FIG. 10;

FIG. 17 shows an embodiment with a deformable grip part in the starting position;

FIG. 18 shows the grip part from FIG. 17 in the extended position;

FIG. 19 shows a further embodiment of a deformable grip part in the starting position;

FIG. 20 shows the grip part from FIG. 19 in the deployed position;

FIG. 21 is a semi-schematic side view of another alternative needle assembly provided in accordance with aspects of the present invention;

FIG. 22 is a semi-schematic cross-sectional side view of the needle assembly of FIG. 21 from a different angle without the tubing;

FIG. 23 is a semi-schematic exemplary partial side view of the needle and the protective element of FIG. 21 shown separated from the needle holder and middle retaining portion for clarity;

FIG. 24 is a semi-schematic perspective view of the needle holder of FIG. 21 without the needle or the hose for clarity;

FIG. 25 is a semi-schematic cross-sectional side view of the needle holder of FIG. 24;

FIG. 26 is a semi-schematic bottom view of the needle holder of FIG. 24;

FIG. 27 is a semi-schematic cross-sectional side view of the middle retaining portion of FIG. 22;

FIG. 29 is a semi-schematic exploded side view of yet another alternative needle assembly provided in accordance with aspects of the present invention;

FIG. 30 is a semi-schematic side view of the needle assembly of FIG. 29 in an assembled state; and FIG. 31 is a semi-schematic cross-sectional side view of the needle assembly of FIG. 30.

DETAILED DESCRIPTION OF THE INVENTION

The detailed description set forth below in connection with the appended drawings is intended as a description of the presently preferred embodiments of protective devices for injection needles provided in accordance with practice of the present invention and is not intended to represent the only forms in which the present invention may be constructed or utilized. The description sets forth the features and the steps for constructing and using the protective devices of the present invention in connection with the illustrated embodiments. It is to be understood, however, that the same or equivalent functions and structures may be accomplished by different embodiments that are also intended to be encompassed within the spirit and scope of the invention. Also, as denoted elsewhere herein, like element numbers are intended to indicate like or similar elements or features.

Figure 1:
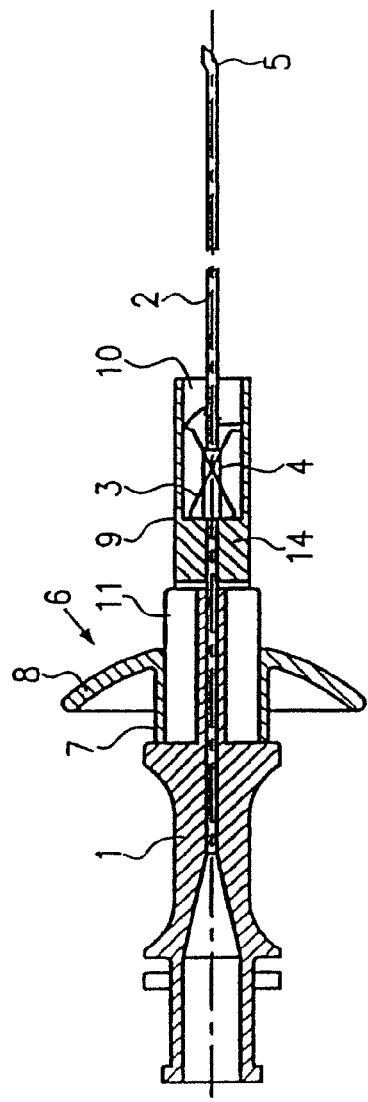
FIG. 1 shows a protective device in longitudinal section.

FIG. 1 shows a needle holder 1 in which a needle 2 is secured. Arranged on the shaft of the needle 2 there is a protective element 3 in the form of a spring clip with intersecting arms. Reference number 4 indicates a sleeve which can be moved with the protective element 3 along the needle shaft. In the illustrative embodiment shown, the tip 5 of the needle is designed with a curve in the manner of an epidural needle or a Huber needle, so that the sleeve 4, which has a smaller diameter than the curve on the needle tip, and, together with it, the protective element 3 and cannot be moved past the needle tip.

Arranged between needle holder 1 and protective element 3 there is a grip part 6 which, at the proximal end, has a hollow cylindrical portion 7 on which a radially protruding shield 8 is formed. On the front face of the shield 8 there is a cylindrical portion 9 whose distal end is hollow. In the standby position according to FIG. 1, the protective element 3 is arranged in the cavity 10 and, by displacement of the grip part 6, can be moved forward to the needle tip 5, while the needle holder 1 is held with the other hand. The angled ends of the intersecting arms of the protective element 3 engage over the needle tip 5, so that injury to operating personnel by the needle tip is prevented.

Figure 2:
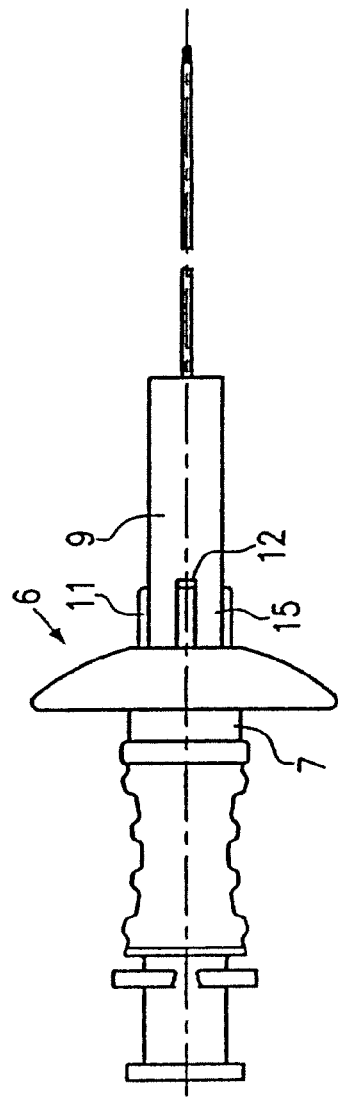
FIG. 2 shows a side view of the embodiment according to FIG. 1.

At the distal end, the needle holder 1 has radially protruding ribs 11 on which the hollow cylindrical portion 7 of the grip part 6 is guided. Between the cylindrical portion 9 of smaller external diameter and the hollow cylindrical portion 7 of greater external diameter, slits 12 are formed in the grip part 6, through which slits 12 the front ends of the ribs 11 of the needle holder 1 protrude radially, as FIG. 2 shows.

The cylindrical portion 9 of the grip part 6 provided with the cavity 10 has a solid cylindrical portion 14 between the slits 12 and the cavity 10, in the central bore of which portion 14 the needle 2 is guided. Between the slits 12 of the grip part 6, the cylindrical portion 9 is connected integrally to the shield 8 and the hollow cylindrical portion 7 via bridges 15.

Figure 4:
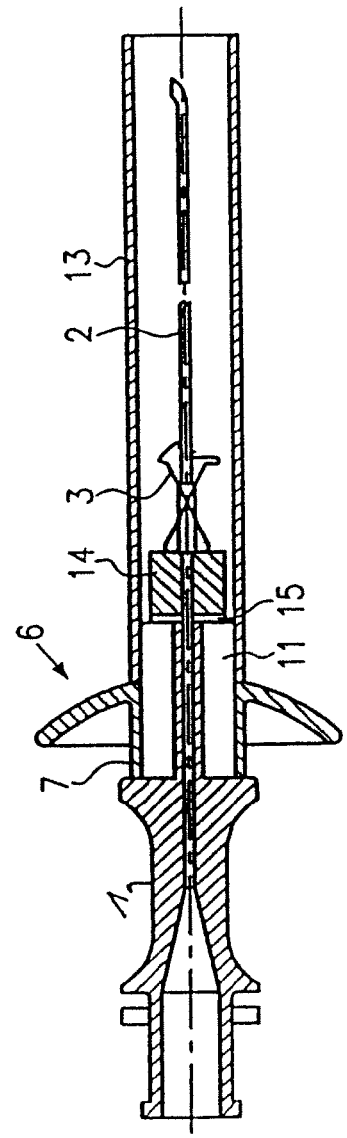
FIG. 4 shows a modified device according to FIGS. 1 and 2 with a needle cap.

These ribs 11 protruding over the outer circumference of the cylindrical portion 9 of the grip part 6 serve for attachment of a needle cap 13, which is shown in FIG. 4. This needle cap 13 is used for storing and handling the device. It can be removed from the needle holder 1 immediately before use of the injection needle, in order to expose the needle, without the grip part 6 and the protective element 3 being moved, because the needle cap 13 is held by the ribs 11 at a radial distance from the portion 9 of the grip part 6.

Because of the smaller diameter at the portion 14 compared to the greater diameter at the ribs 11, the needle cap 13, which consists of a tube section of constant diameter, cannot be positioned incorrectly on the portion 14, but only attached to the ribs 11. This ensures that the needle cap 13 is not inadvertently engaged with a portion of the grip part 6. The needle cap 13 can be produced inexpensively by extrusion of a tube, a section of such a tube forming the needle cap 13.

After removal of the needle cap 13, an injection can be carried out in the standby position according to FIGS. 1 and 2. As the needle is pulled back with one hand on the needle holder 1, the grip part 6 on the portion 7 is held with the other hand, so that the protective element 3 is moved into the protection position on the needle tip as a result of the relative movement between grip part 6 and needle 2. This deployed position of the grip part 6 is illustrated in FIG. 3.

Figure 3:
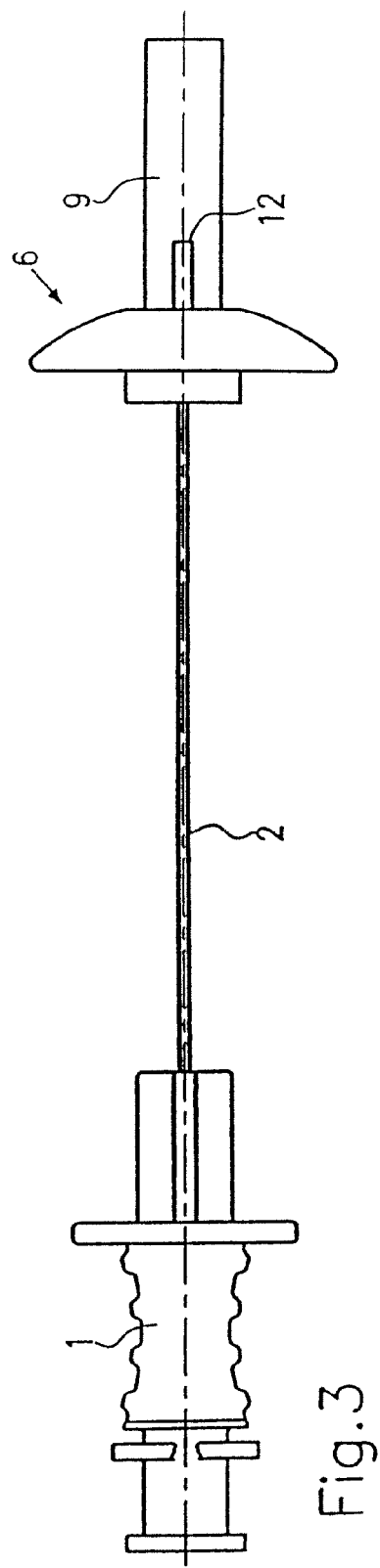
FIG. 3 shows a view of the device according to FIGS. 1 and 2 with the protective element moved to the protection position.

The protective element 3 is arranged loosely in the cavity 10 of the grip part 6, so that the grip part 6 can be easily drawn back from the position in FIG. 3, while the protective element remains in the protection position on the needle tip. The cavity 10 in the cylindrical portion 9 protects the protective element 3 after removal of the needle cap 13.

FIG. 4 shows a preferred embodiment of the grip part 6, the hollow cylindrical portion at the distal end of the grip part 6 being omitted, so that the solid cylindrical portion 14 forms the distal end of the grip part 6. After removal of the needle cap 13 from the ribs 11, the protective element 3 lies free in FIG. 4.

In the embodiment according to FIGS. 1 and 2, the hollow cylindrical portion 7 on the grip part 6 is used to protect the fingers of the hand holding the grip part from touching the needle shaft when the needle is drawn back.

In another configuration of the needle holder 1, this hollow cylindrical portion 7 can be made larger behind the shield 8.

The grip part 6, like the needle holder 1 too, is expediently made of plastic.

Figure 5:
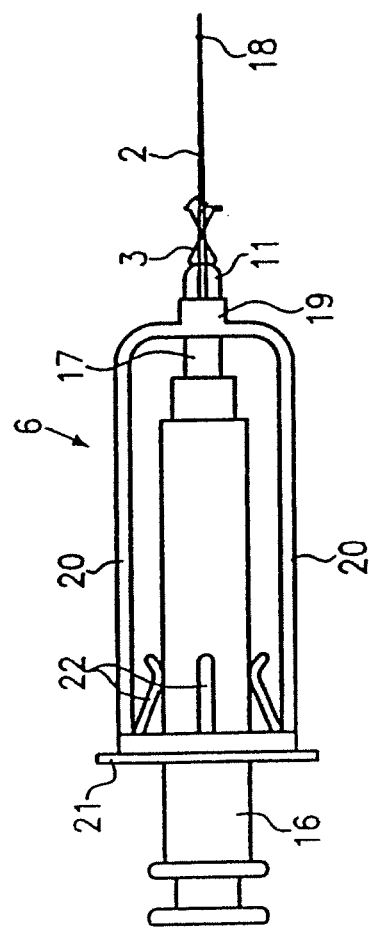
FIG. 5 shows another embodiment of a grip part in conjunction with a syringe.

FIG. 5 shows a modified embodiment of a grip part 6 in combination with a syringe 16 on which an injection needle 2 is secured via a needle holder 17 designed as cannula attachment. In this embodiment, a bead 18 is formed on the outer circumference of the needle, before the needle tip, on which bead 18 the rear wall of the protective element 3 comes to bear in the protection position. Instead of a bead 18, diametrically opposite knob-like projections can be formed by pinching the needle.

The grip part 6 has a cylindrical portion 19 which, in the starting position according to FIG. 5, is guided on the needle holder 17. In the illustrative embodiment shown, two brackets 20 extend from this cylindrical portion 19 in the proximal direction, on diametrically opposite sides, at a distance from the syringe circumference. The ends of these brackets 20 are integrally formed on an annular body 21 from which elastic fingers 22 extend radially inward. The free ends of these elastic fingers 22 lie on the outer circumference of the syringe 16.

Because of the elastic fingers 22 between the grip part 6 and the outer circumference of the syringe 16, the grip part 6 can be used for different sizes of syringe diameter, e.g. syringes with a volume of 1 ml to 10 ml can be fitted into the same grip part. By this means, there is a wide choice of syringes which can be used with the same needle.

In the embodiment according to FIG. 5 too, radially protruding ribs 11 are formed at the front end of the needle holder formed as cannula attachment and these serve as a seat for a needle cap. The protective element 3, whose rear wall protrudes beyond the cross section of the ribs 11, is moved forward into the protection position through the inner circumference of the cylindrical portion 19.

Figure 6A:
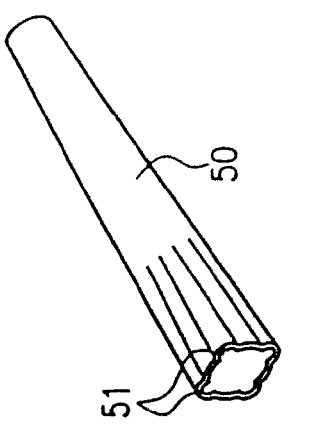
FIG. 6 shows a modified embodiment of the device according to FIG. 5.
Figure 6:
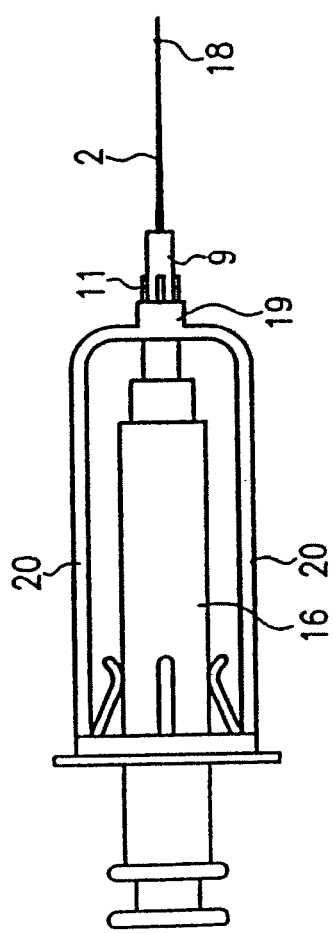

FIG. 6 shows an embodiment of the grip part 6 in which, formed on the cylindrical portion 19, there is a further cylindrical portion 9 in whose cavity 10 the protective element 3 is received. As in the embodiment according to FIGS. 1 and 2, axially extending slits are formed between cylindrical portion 19 and portion 9, through which slits the ribs 11 formed on the needle holder or cannula attachment 17 protrude in order to receive the needle cap 13.

FIG. 6a shows, in a perspective view, a needle cap 50 which is formed by injection-molding and whose distal end can be closed, while the proximal end has, on the inner circumference, flutes or grooves 51 which correspond to the number of ribs 11 and which engage with the ribs 11 when the needle cap is placed on the needle holder 17, so that, by turning the attached needle cap 50, the needle holder 17 can also be turned. A threaded engagement is usually provided between needle holder 17 and syringe 16, so that, by turning the needle cap 50, the needle holder 17 can be screwed onto the syringe 16.

It is customary to draw liquid into the syringe by means of a needle of relatively large diameter and then to replace this needle with a needle having a relatively small diameter, in order to perform an infusion on the patient. In the embodiment according to FIGS. 5 and 6, the needle can be changed without difficulty.

The described design permits actuation with one hand when the syringe content has been injected, the syringe 16 being held with two fingers and the needle being pulled from the patient's skin, while at the same time a finger of the hand bears on the annular body 21 lying at the proximal end.

FIG. 7 shows a plan view of a needle holder 1 which is provided with laterally protruding wings 23 and to which a connection tube 24 is attached. Arranged between the protective element 3 arranged on the needle shaft and the needle holder 1 there is a grip part 6 with a hub-shaped portion 26 which, because of the flat injection angle (FIG. 8), expediently has a surface part 25 for bearing on the patient's skin which, on the bearing side, can be provided for example with an adhesive layer for better retention on the skin. A foam material 25' is preferably provided on the bearing side. The hub portion 26 of the grip part 6 protruding from the front end of the surface part 25 at least partially covers the protective element 3. The surface part 25 or the soft bearing part 25' also serves as spacer for keeping the protective element 3 from the patient's skin. In the illustrative embodiment according to FIG. 8, the soft bearing part 25' extends across the surface part 25 under the hub portion 26, so that the protective element 3 does not lie on the patient's skin.

The needle holder 1 provided with wings 23 is used for venous infusions, for which a thin needle is normally used. The wings 23 are relatively large and flexible. They are pressed together if the needle is introduced into the skin at a very flat angle. A protective paper (not shown) applied on the adhesive layer on the bearing surface should not be peeled off until the needle is introduced into the vein. After the needle has been introduced into the vein, the wings 23 are placed flat against the patient's skin and secured with an adhesive tape. The grip part 6 too can be secured by means of an adhesive tape, the hub-shaped portion 26 preventing contact between protective element 3 and adhesive tape. When the needle is drawn back after removal of the adhesive tape from the needle holder, the grip part 6 initially remains in its position with the protective element 3. After the drawn-back needle tip is safely covered by the protective element 3, with the projections 18 on the needle fixing the protective element 3 on the needle tip, the grip part 6 can also be removed from the patient's skin.

FIGS. 7 and 8 show the device in the standby position for insertion of the needle. If the bearing surface 25 provided with an adhesive layer is used on the grip part, this is a passive system.

FIG. 9 shows a view of the grip part 6 from the right in FIG. 7. The wings 23 serve as bearing surface for the needle holder 1 since the infusion needle must remain for a certain time in the inserted position.

FIGS. 10 and 11 show, in a construction according to FIGS. 7 through 9, a needle cap 13 provided with two spaced-apart retaining brackets 27 which are hooked via a curved free end 27' on the wings 23, as FIG. 10 shows. In this embodiment, the proximal end of the needle cap 13 expediently bears on the front end of the protective element 3, as FIG. 10 shows, so that the protective element 3 is held in its standby position.

It is also possible, however, to provide a hub-shaped attachment at the proximal end of the needle cap 13, which attachment bears on the front face of the hub-shaped portion 26.

In the embodiments described, a protective element in the form of a spring clip with intersecting arms is depicted in each case. However, another design of a protective element can also be used in conjunction with the grip part 6.

Figure 12:
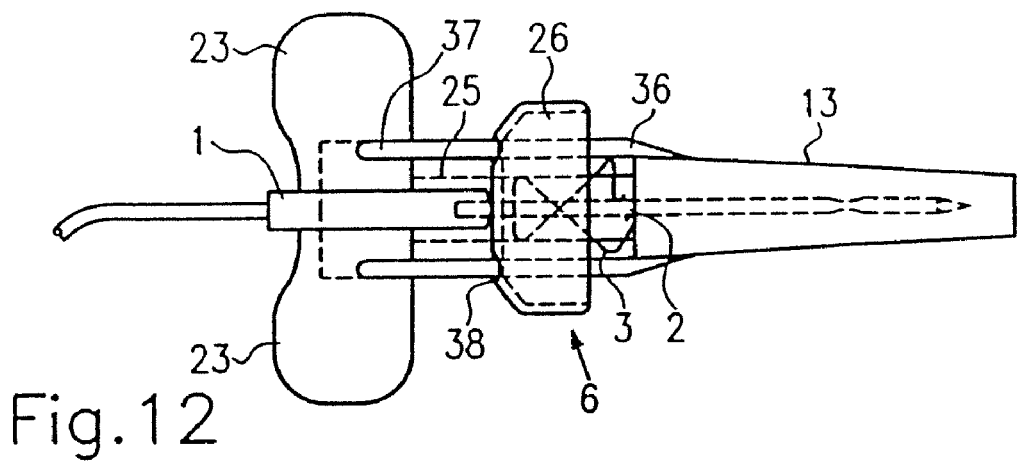
FIG. 12 shows a plan view of an embodiment according to FIG. 7 with a modified needle cap.
Figure 13:
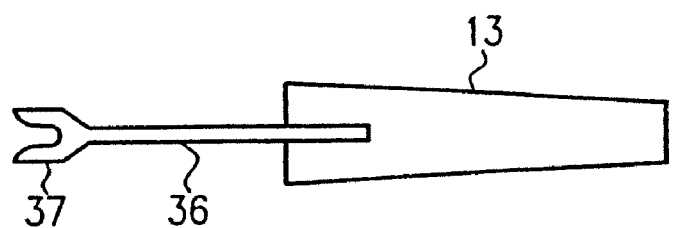
FIG. 13 shows a side view of the needle cap according to FIG. 12.

FIG. 12 shows a further embodiment of the device according to FIGS. 7 through 9. Instead of having the suspension brackets 27, the needle cap 13 is in this case provided on both sides with an extension strut 36 which, at the free end, has a fork-shaped portion 37 for attachment to the wings 23 of the needle holder (FIG. 13). These two spaced-apart struts 36 extend through correspondingly dimensioned openings 38 in the hub portion 26 of the grip part 6, so that the fork-shaped insertion portions 37 can be pulled without difficulty through these openings 38. When the needle cap 13 is taken off, the needle holder 1 is held, and the grip part 6 is not moved.

Figure 14:
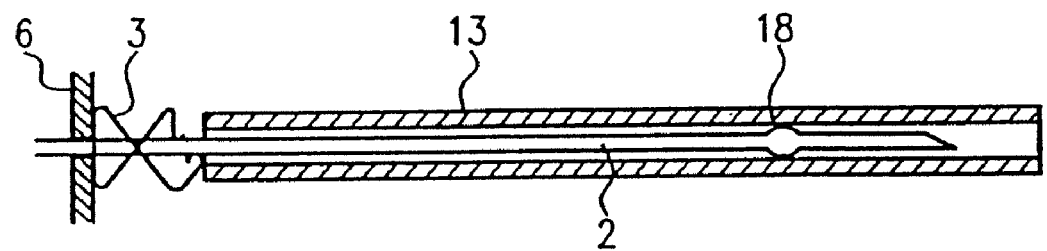
FIG. 14 shows a longitudinal section through a needle cap.

FIG. 14 shows a longitudinal section through a needle cap 13 whose proximal end bears on the protective element 3. The needle cap is of tubular design, and the diameter enlargement 18 on the needle 2, produced by pinching, serves as a spacer for the needle cap 13. Such a needle cap can be produced by extrusion or injection-molding. It is also possible to form, on the inner circumference of the needle cap, a bead or knobs, which bear on the needle shaft and guide the needle substantially concentrically in the needle cap. The needle cap 13 is in this case held on the needle 2 by friction on the bulges 18.

According to a further embodiment, the needle cap, when it has been fitted onto the needle, can be fixed on the needle by mean of heat and pressure or by shrinking.

Figure 15:
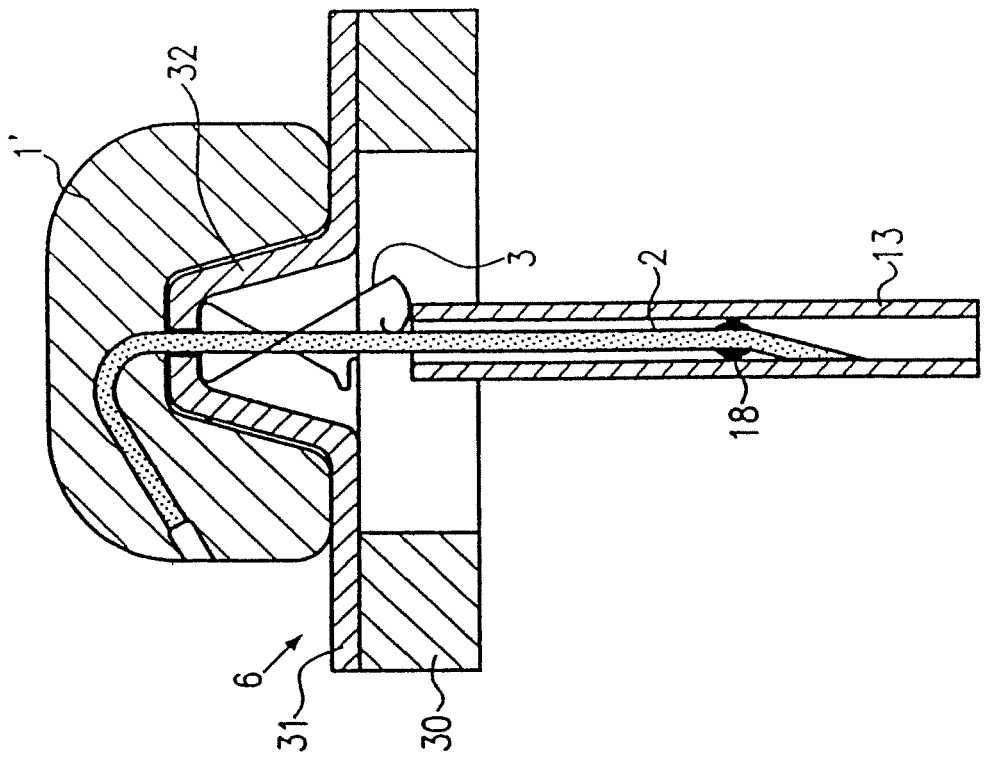
FIG. 15 shows a cross section through another embodiment with a curved needle.

FIG. 15 shows an embodiment in combination with a Huber needle 2 which is held in a needle holder 1' by means of a curved portion and is provided for perpendicular insertion upon injection. Reference number 30 designates a bearing part which is preferably made of foam material and which is provided with an adhesive face for better fixing on the patient's skin. Arranged between the bearing part 30 and the needle holder 1' there is a shield-like grip part 6 which rests on the bearing part via a flange-like area 31 and extends via a pot-shaped middle portion 32 into a corresponding depression in the needle holder 1'. The protective element 3 is arranged in this pot-shaped middle part 32.

When the needle is drawn out, the grip part 6 is held on the bearing part 30, while the needle holder 1' is removed. The protective element 3 is moved toward the needle tip until it comes to rest on the needle bulge 18, while at the same time the two intersecting arms of the protective element 3 engage over the needle tip and cover it. The grip part 6 can be removed from the bearing part 30 or together with the latter. Grip part 6 and bearing part 30 can also be connected to one another via an adhesive layer.

The side walls of the pot-shaped middle part 32 are preferably conical so that the grip part 6 cannot itself be removed but instead only pressed.

FIG. 15 shows a needle cap 13' with a tubular portion from whose proximal end there protrude diametrically opposite wall portions 33 which are inserted via partially circular slits 34 in the flange 31 of the grip part 6 into correspondingly partially circular grooves 35 in the needle holder 1'. The curved wall portions 33 are guided loosely through the curved slits 34 in the flange 31 of the grip part 6 and inserted with a press fit into the grooves 35 of the needle holder 1'.

As in the other embodiments of a needle cap 13, the needle cap 13' in FIG. 15 can also be closed at the distal end.

Figure 16:
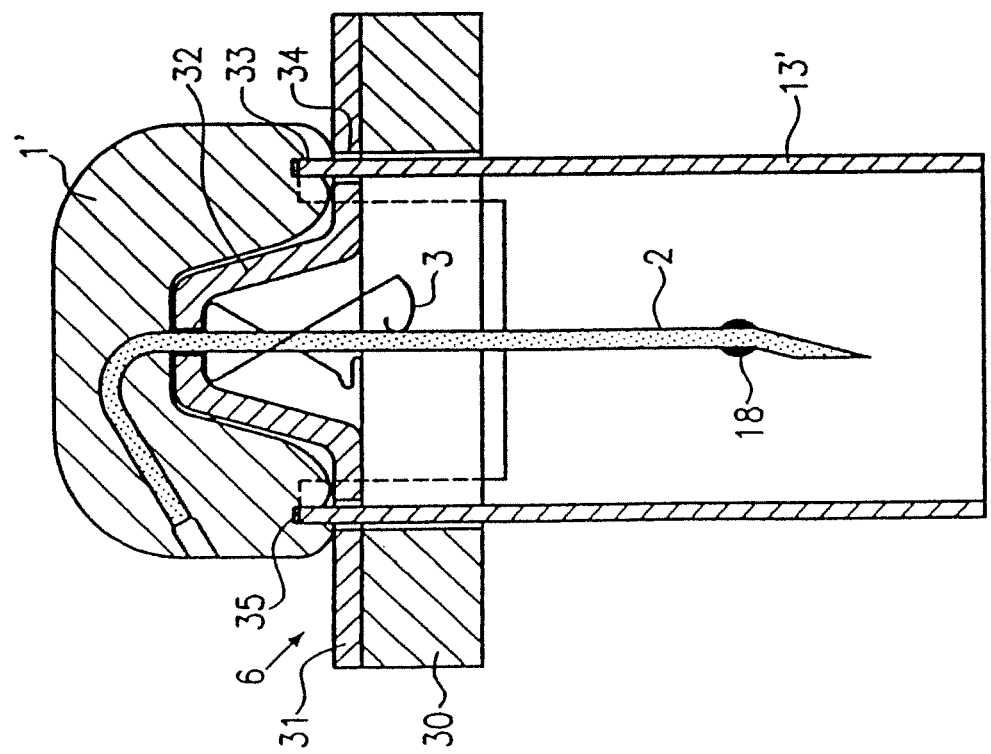
FIG. 16 shows another needle cap in the embodiment according to FIG. 15.

FIG. 16 shows an embodiment with a Huber needle 2 according to FIG. 15, where a needle cap 13 of smaller internal diameter is pushed onto the needle 2. The needle cap corresponds substantially to that of FIG. 14, the needle cap 13 being held on the needle by means of friction at the angled front end. This needle cap 13 in FIG. 16 can be provided with radially protruding and diametrically opposite surface portions 52 through which handling is improved and the tubular needle cap 13 is made more rigid. FIG. 16a shows a perspective view of such a needle cap 13 with diametrically opposite surface portions 52.

FIGS. 17 and 18 show an embodiment in which the grip part 6 has a deformable portion by means of which the distal end of the grip part, on which the protective element 3 lies, can be moved in the direction of the protection position on the needle tip by means of the deformable portion being deformed. In the illustrative embodiment according to FIGS. 17 and 18, two pairs of deformable brackets 40 and 40' are formed on the grip part 6 and these can be pressed together by the fingers so that they can be moved from the curved state in FIG. 17 to an extended state in FIG. 18. The two deformable pairs of brackets 40 and 40' are connected to one another by a sleeve portion 41. It is also possible to insert, between the two bracket pairs 40 and 40', an element which, when pressed by the fingers, changes the two deformable brackets 40 and 40' to the extended position according to FIG. 17.

FIGS. 19 and 20 show a further embodiment of a deformable grip part 6, FIG. 19 illustrating the grip part in the collapsed state in the standby position. The needle cap 13 is provided at the proximal end with a receiving portion 42 which receives collapsed portions 45 of the grip part 6, which is arranged between needle holder 1 and the protective element 3 (not shown in FIG. 19) arranged in the receiving portion 42.

FIG. 20 shows in schematic representation the grip part 6 in a partially deployed state after the needle cap 13 has been removed and an injection has been carried out. The stiff portions 45 of the grip part 6 which are connected to one another via articulations and hinge portions 44 and which are partially guided on the needle 2 are moved and aligned along the needle, the protective element 3 being pushed forward to the needle tip until it engages with the needle bulge 18 and covers the needle tip.

Compared to the embodiments according to FIGS. 17 through 20, the embodiments according to FIGS. 1 through 16 have the advantage that a greater cannula length is available in the standby position because the protective element 3 lies directly on the needle holder, whereas, in the embodiments according to FIGS. 17 through 20, a more complicated design of the grip part 6 is provided between protective element 3 and needle holder 1, as a result of which the available cannula length is restricted. The embodiment according to FIGS. 19 and 20 is also more advantageous in terms of the length of the available cannula than the embodiment according to FIGS. 17 and 18 because a more compact arrangement is made possible by the folding of the portions 45, as FIG. 19 shows when compared to FIG. 17. Instead of the fold portions in FIG. 20, a scissor mechanism between protective element and needle holder can also be provided in order to accommodate, in a smaller space, elements with which the protective element can be deployed.

Figure 14A:
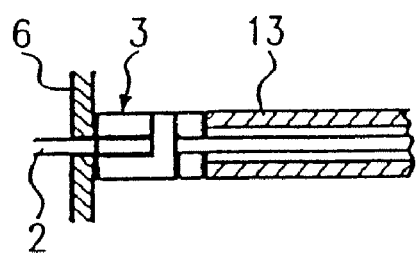

In all the embodiments, the protective element 3 is preferably a needle clip which is made of metal and whose intersecting arms issue from opposite sides of a proximal wall portion having a hole for the passage of the needle, the hole diameter being smaller than the maximum transverse dimension of the needle at the pinch 18, so that the needle clip is held in the protection position on the needle tip by means of the portion 18 of increased diameter. The intersecting arms extending on both sides of the needle 2, as FIG. 14a shows, have, at the distal end, an end portion which is widened to approximately the width of the rear wall and which, in the starting position, lies with elastic pretensioning on the outer circumference of the needle and, on reaching the needle tip, is moved by spring action into the protection position in which the two widened end portions engage over the needle tip. For this purpose, the distal ends of the arms, as the side views show, are slightly offset with respect to one another in the longitudinal direction or the arms are of different lengths, so that it is thus ensured that the two angled end portions of the arms engage over the needle tip. At least on the longer arm, the end portion is curved inward at the free edge in order to ensure that the needle tip is covered even if an attempt is made to push the needle clip back from the protection position on the needle, the inwardly curved end portion hooking onto the needle tip. The needle clip as a whole can be made very compact and only about 7 mm long.

Referring now to FIG. 21, a semi-schematic side view of an alternative safety Huber needle assembly 50 is shown comprising a needle holder 52 and a middle retaining portion 54 received by the needle holder. The middle retaining portion 54 comprises a flange 31, which has a bore for receiving a Huber needle 2. An optional safety sleeve or Huber guard 56 made from a plastic material, such as a polyurethane material, is positioned over the Huber needle 2 to cover the needle tip 58 of the Huber needle. The Huber guard 56 comprises a central cylindrical section 60 and a pair of fins 62a, 62b extending from the central cylindrical section in opposing configuration.

As further discussed below, the Huber needle 2 is attached to a needle holding sleeve 64 of the needle holder 52, which has a lumen in fluid communication with the lumen of the Huber needle. In one exemplary embodiment, a medical grade plastic tubing 65 made from DEHP free PVC is attached at its first end 66 to an outlet end 103 (FIG. 22) of the needle holding sleeve 64 and at its second end 68 to a female Luer lock adapter 70. A screw cap 72 is threadedly engaged to the female Luer lock adapter 70 to preserve sterility until use. A tubing clamp 74, such as those offered by Halkey-Roberts of St. Petersburg, Fla., is disposed on the tubing 65 for isolating or clamping the tubing when desired.

FIG. 22 is a semi-schematic cross-sectional side view of the Huber needle assembly 50 of FIG. 21 from a reverse angle without the tubing 65 for clarity. As shown, the Huber needle 2 is attached to the needle holder 52 by means of a section of the needle proximal of a bent section 76 inserted into the inlet end 78 of the needle holding sleeve 64 and, in one embodiment, fixed in place by adhesive or glue. In the Huber needle ready to use position (FIGS. 21 and 22), at least a portion of the middle retaining portion 54 is received in the interior cavity 80 of the needle holder 52. In one exemplary embodiment, a tubular extension 82 of the middle retaining portion 54 extending from the base or flange 31 comprising an exterior surface 84 and an interior surface 86 extends into the interior cavity 80 of the needle holder 52. As further discussed below, the exterior surface 84 of the tubular extension 82 engages the surface of the interior cavity 80 of the needle holder 52 to maintain the two in removable engagement when in the ready to use position.

The interior surface 86 of the middle retaining portion 54 defines a retaining bore 88 adapted to pass the Huber needle 2 therethrough and to retain the protective element 3 therein. In one exemplary embodiment, this retaining configuration is implemented by incorporating a bump 85 comprising a reduced diameter section $D_r$ that is nominally smaller than an inside diameter dimension $D_{id}$ of the retaining bore 88, at either end or opening of the retaining bore. With reference to FIGS. 22 and 23, when the protective element 3 is in the ready to use position (FIGS. 22 and 23, top), the arms 92a, 92b (FIG. 23) are biased radially apart by the curved tips 94a, 94b abutting the side of the Huber needle 3. In this position, the dimension D2 measured from one intersecting joint 96a to another intersecting joint 96b is larger than the same measurement D1 measured when the arms 92a, 92b are in a relaxed state (i.e., not abutting the side of the needle) and the fingers 98a, 98b overlapped (FIG. 23, bottom). In one exemplary embodiment, the reduced diameter section $D_r$ is larger than D1 but is smaller than D2, which is smaller than $D_{id}$. Expressed mathematically, the diameters have the following relationship: $D1<D_r<D2<D_{id}$. Alternatively, D2 can be equal to $D_{id}$ or slightly larger than $D_{id}$ as the fingers 98a, 98b are able to flex when positioned inside the retaining bore 88 and slide past the bump 85.

The Huber needle assembly 50 may be placed in the ready to use position by first positioning the protective clip 3 over the Huber needle 2 and then sliding the Huber needle through the retaining bore 88 of the middle retaining portion 54. The Huber needle 2 may include a bulge or a crimp 91 for stopping the forward movement of the protective clip 3 when the opening 93 of the clip, which is smaller than the crimp 91, abuts the crimp. As the tubular extension 82 of the middle retaining portion 54 moves into the interior cavity 80 of the needle holder 52, the portions adjacent the interconnecting joints 96a, 96b of the protective clip 3 abuts the reduced diameter section $D_r$ of the retaining bore 88. Further downward movement of the needle holder 52 relative to the middle retaining portion 54 causes the protective clip 3 to flex and the fingers 98a, 98b move past the reduced diameter portion $D_r$ into the ready to use position. The relative movement stops when the upper end surface 100 of the middle retaining portion 54 abuts the interior surface of the interior cavity 80 of the needle holder 52.

FIG. 24 is a semi-schematic perspective view of the needle holder 52 without the Huber needle 2. The needle holder 52 comprises a central needle base structure 102 having the needle holding member 64 extending therefrom with an outlet 103. If the base 104 of the needle holder 52 defines a plane, preferably the needle holder member 64 extends at an angle relative to the plane, although not necessary (i.e., parallel to the plane). In one exemplary embodiment, the needle holder member 64 extends at about a 0 to about a 90 degree angle relative to the plane with 45 degrees being more preferred.

The angled configuration facilitates running a tubing along a patient's skin, such as in the manner shown in FIG. 21.

A shroud 106 extends on each side of the central needle base structure 102 forming part of an enclosure or housing of the needle holder 52. In one exemplary embodiment, the shroud 106 comprises a plurality of gripping members 108 for facilitating gripping the needle holder 52, although a flat or smooth surface may also be incorporated. An optional pair of fins 110 may be incorporated in the needle holder 52, one fin over each shroud 106. A pair of ledges 111 (FIGS. 25 and 26) extend from the base of the shrouds 106 and of the fins for added reinforcement, although not required. In one exemplary embodiment, the shrouds 106 can have an upper surface 112 (FIG. 24) that is generally flushed or even with the upper surface 114 of the central needle base structure 102. Accordingly, many alterations may be made to the structure and features of the needle holder 52 without deviating from the sprit and scope of the present invention.

A gap or channel 116 is provided intermediate the two shrouds 106. The channel 116 runs or extends a portion of the top surface of the needle holder 52 and the entire length of the front side opposite the central needle base structure 102. For assembling or making the needle holder 52, the channel 116 facilitates insertion of the blunt end of the Huber needle 2 into the inlet end 78 of the needle holding member 64 as the gap defined by the channel provides access into the interior cavity 80 of the needle holder 52. Alternatively, the channel 116 can extend a portion of the length of the front side opposite the central needle base structure 102 and a portion of the top surface of the needle holder 52 and still provide for access to the interior cavity 80 for mounting the Huber needle 2.

FIG. 25 is a semi-schematic cross-sectional side view of the needle holder 52 of FIG. 24 taken along a lengthwise direction. The interior cavity 80 of the needle holder 52 comprises a main interior section 118, a secondary interior section 120, and a secondary slot 122 adjacent the main interior section 118, which forms part of the channel 116. As further discussed below, the main interior section 118 is configured to receive the tubular extension 82 of the middle retaining portion 54 and either one of the secondary interior section 120 or secondary slot 122 is configured to receive an orientation marker 124 (FIG. 27) to angularly align the middle retaining portion 54 to the needle holder 52.

An inwardly extending protrusion 126 is incorporated on each interior surface of each shroud 104. The inwardly extending protrusion 126 may comprise a single continuous anchor or projection extending along at least a portion of the interior surface of the shroud 104 at the main interior section 118 or may alternatively comprise two or more individual anchors on the interior surface of each shroud 106. The inwardly extending protrusion 126 is configured to snap or mate with a groove 128 (FIG. 27) on the tubular extension 82 to removably secure the middle retaining portion 54 to the interior cavity 80 of the needle holder 52 in a detent-type engagement when in the ready position.

FIG. 26 is a semi-schematic bottom view of the needle holder 52 of FIG. 24. In the configuration shown, the main interior section 118 of the interior cavity 80 is semi-frustoconical in shape, in view of the gaps 120, 122, with the interior surface 130 of the main interior section 118 having a slight taper that tapers inwardly from about the base 104 towards the top 105. However, a straight wall surface without a slight taper may be incorporated. Side wall portions 132 of the central needle base structure 102 extend at an angle from the back wall 134 of the central needle base structure 102 to create a generally rectangular secondary interior section 120 of the interior cavity 80. However, this secondary interior section 120 may incorporate other configurations by changing the contour or shape of the side wall portions, such as a square or a curved structure.

FIG. 27 is a semi-schematic cross-sectional side view of the middle retaining portion 54 provided in accordance with aspects of the present invention. In the figure shown, the orientation marker 124 is attached to the tubular extension 82 via a webbing 136, which is similar to a rib and, in one embodiment, is integrally molded with the flange 31, the orientation marker 124, and the tubular extension 82. The orientation marker 124 is configured to fit into the secondary interior section 120 of the interior cavity 80 or the secondary slot 122 when the middle retaining portion 54 is removably mated to the needle holder 52. The middle retaining portion 54 may be made from polyethylene or similar plastics and may be enhanced with color, such as a light green or other desired colors. A plurality of openings (not shown) may be incorporated in the base 31 of the middle retaining portion 54 to facilitate taping the base to the patient. The openings can vary in shapes, sizes, and numbers and can also be eliminated.

Figure 28:
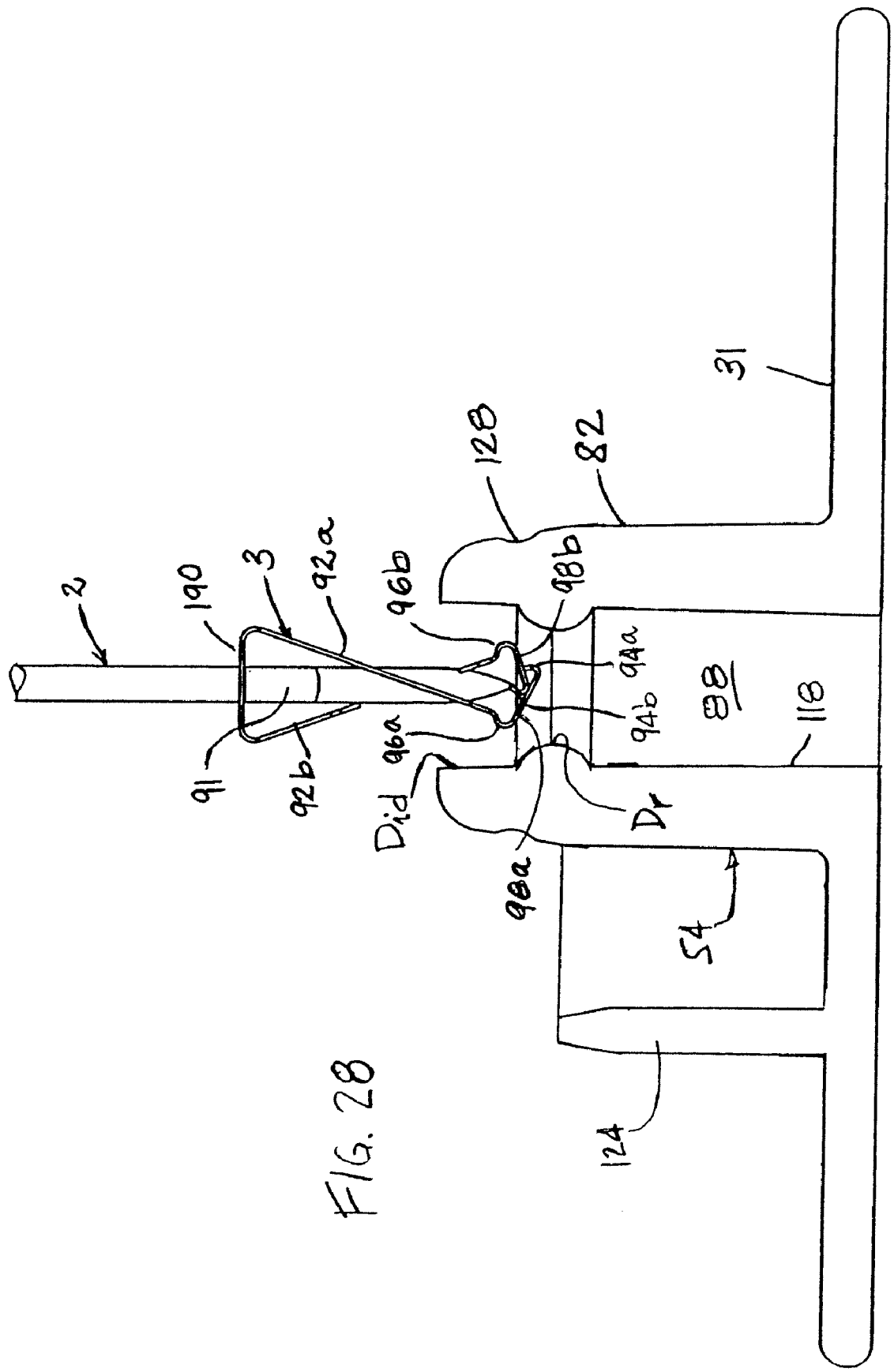
FIG. 28 is a semi-schematic partial cross-sectional side view of the protective element activated over the needle and separated form the middle retaining portion.

Referring now to FIG. 28 in addition to FIG. 22, the alternative needle assembly 50 may be used by first removing the safety sleeve 56 from the Huber needle 2. The needle 2 is then inserted into a subject until the flange 31 abuts the subject. When the injection is completed, the needle 2 may be withdrawn from the subject and the needle tip shielded by the protective clip 3 by holding onto the flange 31 while concurrently retracting the needle 2 proximally or away from the subject. During this proximal needle motion, the intersecting joints 96a, 96b of the needle clip 3 abut the reduced diameter section $D_r$ of the main internal section 118 of the interior cavity 80 of the middle retaining portion 54 to permit the needle to move relative to the protective clip 3. As previously discussed, this relative movement is provided due to the larger clip dimension D2 (FIG. 23) when the curved lips 94a, 94b of the needle clip 3 abut the side of the needle 2 as compared to the reduced diameter section $D_r$ of the interior cavity 80.

When the needle tip moves proximal of the curved lips 94a, 94b of the needle clip 3 so that the needle clip 3 is no longer biased by the needle (FIGS. 23, bottom, and 28), the resilient arms 92a, 92b are unrestrained and flex radially inwardly over the needle tip. This radial movement causes the measurement of the two intersecting joints 96a, 96b (FIG. 23) to decrease from D2 to D1 while at the same time allows the fingers 98a, 98b to overlap over the needle tip to shield the needle tip. As the measurement D1 between the two intersecting joints 96a, 96b is now smaller than the reduced diameter section $D_r$ of the interior cavity 80, the needle clip 3 is able to slip past the reduced diameter section $D_r$ of the bore 88 when the needle 2 is further moved proximally (FIG. 28). The needle clip 3 is now attached to the needle 2 and separates from the middle retaining portion 54 (FIG. 28).

FIGS. 29-31 show another alternative needle assembly 140 provided in accordance with aspects of the present invention in various views and state of assembly. Referring initially to FIG. 29, the needle assembly 140 comprises a needle hub 142, a needle 144 having a protective clip 3 positioned thereon attached at its proximal end to the distal end 146 of the needle hub 142, a middle retaining portion 148, and a needle cover 150. The needle hub 142 comprises a base section 152 having a Luer lock 154 and a transition section 156 that connects to a nose section 158 having a nose flange 160 positioned thereon. A plurality of spaced apart ribs 162 are formed along the exterior surface of the hub, which in one exemplary embodiment comprises four ribs evenly spaced along the exterior surface although no ribs, fewer ribs, or more ribs may be included without deviating from the spirit and scope of the present invention.

The nose section 158 further comprises an alignment plate 164, which in one exemplary embodiment is an extension of one of the ribs distal of the nose flange 160. The alignment plate 164 cooperates with a notch on the middle retaining portion 148 to angularly align the middle retaining portion to the needle hub 142, as further discussed below. An end flange 166 is incorporated at the distal end 146 of the nose section 158 having a diameter larger than the diameter of the nose section 158. Preferably the diameter of the end flange 166 is approximately the same as the inside diameter of the middle retaining portion 148 for size-on-size or frictional engagement with the inside diameter of the middle retaining portion (FIG. 31). Alternatively, the end flange 166 may be eliminated and the nose section 158 sized to form a size-on-size or friction fit with the interior surface of the middle retaining portion 148. Still in another alternative embodiment, the fit between the middle retaining portion 148 and the end flange 166 or the nose section 158 is a slight loose fit for easy operability of the middle retaining portion from a ready to use position to an activated position.

The needle clip 3, which is the same as the needle clip described above (See, e.g., FIG. 23), is positioned on the needle 144. The needle clip 3 is configured to move from a proximal position on the needle 144 to a distal position on the needle to block the needle tip, as further discussed below. In one exemplary embodiment, a crimp or bump 168 is incorporated near the needle tip to stop the distal movement of the needle clip 3. However, a clip that frictionally engages with the needle shaft in the absence of the crimp or bump may also be used with the present needle assembly, as well as other needle assemblies described elsewhere herein.

The middle retaining portion 148 is configured to retain the needle clip 3 at the proximal end of the needle when in a ready to use position (FIGS. 30 and 31) and move the needle clip to a blocking position when activated. In one exemplary embodiment, the middle retaining portion 148 comprises a rear flange 170, a tubular body 172, which may include a generally tapering cylinder or other shaped bodies, and a gripping flange 174. In one exemplary embodiment, the gripping flange 172 comprises two separate upper and lower projections. However, a continuous circular flange, a continuous square flange, other shaped flanges, or no flange may be incorporated. The gripping flange 174 facilitates gripping by a user in moving the middle retaining portion 148 distally to activate the protective clip 3 over the needle tip.

The needle cover 150 comprises a base section 176 and a protective section 178. The base section 176 is configured to removably engage with the nose flange 160 on the needle hub 142 while the protective section 178 is configured to shield the needle and needle tip prior to usage of the needle. In one exemplary embodiment, the base section 176 comprises an opened lower section 180 and a pair of grooves or detents on an inside interior surface (not shown) of the base section 176. The pair of grooves or detents are configured to latch with the nose flange 160 in a detent-type configuration. In one exemplary embodiment, the needle cover 150 is semi-opaque to permit visual inspection of the needle prior to use.

Referring now to FIG. 30 in addition to FIG. 29, in a ready to use position, the middle retaining portion 148 is telescopically positioned over the nose tip section 182 of the nose section 158. Although the rear flange 170 of the middle retaining portion 148 is shown abut the nose flange 160 of the nose section 158, a slight gap or space is acceptable provided the positioning of the middle retaining portion 148 over the nose section allows the protective clip 3 to slide over a projection or bump inside the middle retaining portion, as further discussed below.

An indicia 184, such as an arrow or a marker, may be incorporated on the middle retaining portion 148 for either aesthetic reasons or for conferring instructions to a user to advance the middle retaining portion in the direction indicated, or both. However, the indicia 184 may be eliminated as the use of the needle assembly 140 is intuitive without the indicia.

FIG. 31 is a cross-sectional side view of the needle assembly of FIG. 30 from a different viewing angle. As shown, the middle retaining portion 142 comprises a bore 186 having an interior surface that includes bump or a reduced diameter section $D_r$, similar in configuration as the middle retaining portion 54 of FIGS. 27 and 28. The bump or reduced diameter section $D_r$ of FIG. 31 cooperates with the protective clip 3 in the same way as the middle retaining portion 54 and needle clip 3 of FIGS. 23-28 to provide the same retaining and relative movement functions. Also shown is a needle hub bore 185, which is configured to receive a Luer tip of a syringe (not shown) or other medical implements.

The protective clip 3 may be moved to a ready to use position by pushing the middle retaining portion 148 over the nose tip section 182 of the needle hub 142. To ensure that the distal portion of the protective clip 3 (See, e.g., the portions comprising the intersecting joints 96a, 96b of FIG. 23) slides past the bump or reduced diameter section $D_r$ of the middle retaining portion 148, the distance between the reduced diameter section $D_r$ and the distal end surface 188 of the nose section 158 of the needle hub 142 should be less than the distance between the proximal end wall 190 of the protective clip 3 and the intersection joints 96a, 96b of the protective clip 3 (See, e.g., FIG. 23). Once mounted in the position shown (FIG. 31), the protective clip 3 moves with the middle retaining portion 148 and relative to the needle 3 until the clip is no longer urged by the needle, as further described below and as described above with reference to FIGS. 22 and 28.

A slot or notch 192 is incorporated at the proximal end of the middle retaining portion 142. The notch 192 is configured to receive the alignment plate 164 on the nose section 158 of the needle hub 142 to angularly align the middle retaining portion 148 to the needle hub 142. However, the notch 192 and the alignment plate 164 may be eliminated if angular alignment between the needle hub 142 and the middle retaining portion 142 is not necessary.

The needle assembly 140 may be used by first mounting the needle hub 142 over a syringe or other medical implement and then removing the needle cover 150. A fluid may be aspirated into the syringe via the needle or the needle may be inserted into a subject if a fluid sample from the subject is to be taken. Following the injection, the needle 144 is retracted or withdrawn from the subject (either by pulling on the syringe (not shown) or grabbing the needle hub 142 and pulling on the needle hub away from the subject) with one hand while holding or grabbing onto the middle retaining portion 148 with the other hand.

As the needle is retracted, the protective clip 3 is held by the reduced diameter section $D_r$ of the middle retaining portion 148 and moves relative to the needle 144 until the needle tip moves proximal of the curved lips 94a, 94b (See, FIG. 23, bottom), at which point the protective clip moves radially inwardly such that the fingers 98a, 98b overlap over the needle tip to shield the needle tip. Approximately simultaneously therewith, the cross-sectional dimension of the protective clip 3 at its distal end collapses or reduces in size so that said section of the protective clip is now smaller than the reduced diameter section $D_r$ of the middle retaining portion 148, which then allows the protective clip 3 to separate from the middle retaining portion. The needle and needle hub may then be disposed of pursuant to standard protocols.

Although limited embodiments of the syringe assemblies and their components have been specifically described and illustrated herein, many modifications and variations will be apparent to those skilled in the art. Accordingly, it is to be understood that the syringe assemblies and their components constructed according to principles of this invention may be embodied other than as specifically described herein. The invention is defined in the following claims.

What is claimed is:

1. A needle assembly comprising:
   a needle hub comprising a walled structure having a needle comprising a needle shaft, a needle tip, and an enlarged diameter section near the needle tip;
   a metal clip comprising a proximal wall comprising a perimeter defining an opening having a portion of the needle passing therethrough, a first arm extending distally of the proximal wall and to a first side of the needle shaft, and a second arm extending distally of the proximal wall and to a second side of the needle shaft;
   a grip part configured for being gripped comprising an arm in contact with the metal clip, the arm having a portion that is pivotable about a point in moving from a ready to use position to a protective position; and
   wherein both the metal clip and the arm of the grip part are in contact with the needle shaft, and wherein the opening on the proximal wall is sized to engage the enlarged diameter section to prevent the metal clip from being displaced distally beyond the needle tip.

2. The needle assembly of claim 1, further comprising two or more arms attached to the arm of the grip part and wherein the arm and the two or more arms are attached to one another by a hinge portion.

3. The needle assembly of claim 1, wherein the first arm and the second arm of the metal clip each comprises a radially extending wall at an end opposite the proximal wall.

4. The needle assembly of claim 1, wherein the first arm and the second arm of the metal clip intersect one another.

5. The needle assembly of claim 1, wherein the metal clip is positioned distally of the arm of the grip part.

6. The needle assembly of claim 1, wherein the opening on the metal clip is configured to engage the enlarged diameter section in the protective position.

7. A needle assembly comprising:
   a needle hub comprising a walled structure having a needle comprising a needle shaft, a bulge and a needle tip projecting distally thereof;
   a metal clip comprising a proximal wall comprising a perimeter defining an opening having a portion of the needle passing therethrough, a first arm extending distally of the proximal wall, and a second arm extending distally of the proximal wall, wherein the bulge is sized and configured to impede movement of the proximal wall distally beyond the bulge;
   a grip part configured for being gripped comprising an arm having a portion that is pivotable about a point in moving from a ready to use position to a protective position; and
   wherein at least one of the first arm and the second arm extends from one side of the needle shaft, crosses the needle axis, and to a second side of the needle shaft; and
   wherein the metal clip and the arm are in contact with one another in a protective position.

8. The needle assembly of claim 7, further comprising two or more arms attached to the arm of the grip part and wherein the arm and the two or more arms are attached to one another by a hinge portion.

9. The needle assembly of claim 7, wherein the first arm and the second arm of the metal clip each comprises a radially extending wall at an end opposite the proximal wall.

10. The needle assembly of claim 7, wherein the first arm and the second arm of the metal clip intersect one another.

11. The needle assembly of claim 7, wherein the metal clip is positioned distally of the arm of the grip part.

12. The needle assembly of claim 7, wherein the opening on the metal clip is configured to engage the bulge in the protective position.

13. A needle assembly comprising:
   a needle hub comprising a walled structure having a needle comprising a needle shaft, a bulge and a needle tip projecting distally thereof;
   a metal clip comprising a proximal wall comprising a perimeter defining an opening which allows only a portion of the needle proximal of the bulge to pass therethrough, a first arm extending distally of the proximal wall and to a first side of the needle shaft, and a second arm extending distally of the proximal wall and to a second side of the needle shaft;
   a grip part configured for being gripped comprising an arm in contact with the metal clip, the arm having a portion that is pivotable about a point in moving from a ready to use position to a protective position;
   wherein one of the two arms extends distally of the proximal wall a greater distance than the other one of the two arms; and
   wherein the arm of the grip part is in contact with the needle shaft.

14. The needle assembly of claim 13, wherein the arm of the grip part contacts the needle shaft in the protective position and in a ready to use position.

15. The needle assembly of claim 13, wherein the first arm and the second arm of the metal clip each comprises a radially extending wall at an end opposite the proximal wall.

16. The needle assembly of claim 13, wherein the first arm and the second arm of the metal clip intersect one another.

17. The needle assembly of claim 13, wherein the opening on the metal clip is configured to engage the bulge in the protective position.

* * * * *

UNITED STATES PATENT AND TRADEMARK OFFICE
CERTIFICATE OF CORRECTION

| | |
|---|---|
| PATENT NO. | : 7,608,057 B2 |
| APPLICATION NO. | : 11/609772 |
| DATED | : October 27, 2009 |
| INVENTOR(S) | : Kevin Woehr et al. |

It is certified that error appears in the above-identified patent and that said Letters Patent is hereby corrected as shown below:

Title Page;
On the face page, in field (73), Assignee, in column 1, line 1, delete "Meisungen" and insert -- Melsungen --, therefor.

Signed and Sealed this

First Day of June, 2010

David J. Kappos
*Director of the United States Patent and Trademark Office*